(12) United States Patent
Westphal et al.

(10) Patent No.: US 11,253,493 B2
(45) Date of Patent: Feb. 22, 2022

(54) COMPOSITIONS AND METHODS AFFECTING EXERCISE PERFORMANCE

(71) Applicant: Cliff-Cartwright Corporation, Wellesley Hills, MA (US)

(72) Inventors: Christoph Westphal, Boston, MA (US); Thomas Wessel, Lenox, MA (US)

(73) Assignee: Cliff-Cartwright Corporation, Wellesley Hills, MA (US)

( * ) Notice: Subject to any disclaimer, the term of this patent is extended or adjusted under 35 U.S.C. 154(b) by 0 days.

(21) Appl. No.: 16/479,748

(22) PCT Filed: Jan. 23, 2018

(86) PCT No.: PCT/US2018/014872
§ 371 (c)(1),
(2) Date: Jul. 22, 2019

(87) PCT Pub. No.: WO2018/136943
PCT Pub. Date: Jul. 26, 2018

(65) Prior Publication Data
US 2020/0261382 A1    Aug. 20, 2020

Related U.S. Application Data

(60) Provisional application No. 62/449,411, filed on Jan. 23, 2017.

(51) Int. Cl.
| | | |
|---|---|---|
| A61K 31/05 | (2006.01) | |
| A61K 31/11 | (2006.01) | |
| A61K 31/165 | (2006.01) | |
| A61P 21/00 | (2006.01) | |
| A61K 9/00 | (2006.01) | |
| A61K 31/12 | (2006.01) | |

(52) U.S. Cl.
CPC .......... *A61K 31/165* (2013.01); *A61K 9/0053* (2013.01); *A61K 9/0095* (2013.01); *A61K 31/11* (2013.01); *A61K 31/12* (2013.01); *A61P 21/00* (2018.01)

(58) Field of Classification Search
CPC ................................ A61K 31/05; A61K 31/11
USPC .................................................. 514/701, 731
See application file for complete search history.

(56) References Cited

U.S. PATENT DOCUMENTS

| | | |
|---|---|---|
| 4,313,958 A | 2/1982 | LaHann |
| 4,424,205 A | 1/1984 | LaHann et al. |
| 4,493,848 A | 1/1985 | LaHann et al. |
| 4,532,139 A | 7/1985 | Janusz et al. |
| 4,544,668 A | 10/1985 | Janusz et al. |
| 4,544,669 A | 10/1985 | LaHann et al. |
| 4,564,633 A | 1/1986 | LaHann et al. |
| 4,599,342 A | 7/1986 | LaHann |
| 4,812,446 A | 3/1989 | Brand |
| 5,221,692 A | 6/1993 | Chen |
| 5,290,816 A | 3/1994 | Blumberg |
| 5,403,868 A | 4/1995 | Reid et al. |
| 5,762,963 A | 6/1998 | Byas-Smith |
| 5,962,532 A | 10/1999 | Campbell et al. |
| 6,022,718 A | 2/2000 | Iwai et al. |
| 6,274,177 B1 | 8/2001 | Wu et al. |
| 6,534,086 B1 | 3/2003 | Krumhar |
| 7,407,950 B2 | 8/2008 | Dubois et al. |
| 7,429,673 B2 | 9/2008 | Morazzoni et al. |
| 7,446,226 B2 | 11/2008 | Helsing et al. |
| 7,632,519 B2 | 12/2009 | Jamieson et al. |
| 7,674,594 B2 | 3/2010 | Lee et al. |
| 8,840,938 B2 | 9/2014 | Warnock |
| 9,844,521 B2 | 12/2017 | Kim et al. |
| 9,937,135 B2 | 4/2018 | Bean et al. |
| 10,568,853 B2 | 2/2020 | Bean et al. |
| 2002/0016354 A1 | 2/2002 | Jensen et al. |
| 2003/0031727 A1 | 2/2003 | Hahn et al. |
| 2003/0031737 A1 | 2/2003 | Rosenbloom |
| 2003/0104085 A1 | 6/2003 | Yeomans |
| 2003/0180226 A1 | 9/2003 | Haughton |
| 2003/0185907 A1 | 10/2003 | Krumhar |
| 2005/0085652 A1 | 4/2005 | Chen et al. |
| 2006/0034894 A1 | 2/2006 | Lakkis et al. |
| 2006/0240097 A1 | 10/2006 | Jamieson et al. |
| 2007/0020301 A1 | 1/2007 | Shimagami et al. |
| 2007/0167524 A1 | 7/2007 | Helsing et al. |
| 2007/0293703 A1 | 12/2007 | Chen et al. |
| 2008/0021034 A1 | 1/2008 | Demnitz et al. |
| 2008/0317886 A1 | 12/2008 | Sparkman |
| 2009/0029345 A1 | 1/2009 | Russell et al. |
| 2009/0215107 A1 | 8/2009 | Hwang et al. |
| 2009/0220624 A1 | 9/2009 | Larkins |
| 2009/0304827 A1 | 12/2009 | Kim |

(Continued)

FOREIGN PATENT DOCUMENTS

| | | |
|---|---|---|
| CN | 101040720 A | 9/2007 |
| JP | H09/176002 A | 7/1997 |

(Continued)

OTHER PUBLICATIONS

Notification of Transmittal of the International Search Report and the Written Opinion of the International Searching Authority from corresponding PCT/US2018/014872 dated Mar. 29, 2018.
"Rote Liste 2004" Jan. 1, 2004, Frankfurt/Main pp. 62 090-66 092.
Altman et al. 2001. Arthritis Rheum Nov. 2001;44(11)2531-8. "Effects of a ginger extract on knee pain in patients with osteoarthritis."
Anonymous "Characterizing Soy Sauce" Retrived from the Internet: URL: http://www.kikkomanusa.com/foodmanufacturers/soysaucebasics/characterizingsoysauce.php [retrieved on Jun. 6, 2014].

(Continued)

*Primary Examiner* — Douglas M Willis
(74) *Attorney, Agent, or Firm* — Goodwin Procter LLP

(57) ABSTRACT

Described herein are compositions comprising activators of TRP and ASIC channels that may be useful to improve or preserve exercise performance and exercise recovery.

5 Claims, 4 Drawing Sheets

(56) References Cited

U.S. PATENT DOCUMENTS

| | | |
|---|---|---|
| 2010/0099772 A1 | 4/2010 | Bean et al. |
| 2011/0229590 A1 | 9/2011 | Kim et al. |
| 2011/0305779 A1 | 12/2011 | Cowan |
| 2012/0027693 A1 | 2/2012 | Bean et al. |
| 2012/0128762 A1 | 5/2012 | Chancellor et al. |
| 2013/0197094 A1 | 8/2013 | Moore et al. |
| 2014/0212486 A1 | 7/2014 | Lederman et al. |
| 2014/0343156 A1 | 11/2014 | Bean et al. |
| 2016/0367506 A1 | 12/2016 | Bean et al. |
| 2017/0042834 A1 | 2/2017 | Westphal et al. |
| 2018/0116976 A1 | 5/2018 | Westphal et al. |
| 2019/0038573 A1 | 2/2019 | Westphal et al. |
| 2020/0375925 A1 | 12/2020 | Bean et al. |

FOREIGN PATENT DOCUMENTS

| | | |
|---|---|---|
| WO | 2000/050387 A1 | 8/2000 |
| WO | 2006/0034894 A1 | 4/2006 |
| WO | 2009/071631 A2 | 6/2009 |
| WO | 2009/114139 A2 | 9/2009 |
| WO | 2009/137686 A1 | 11/2009 |
| WO | 2012/015882 A1 | 2/2012 |
| WO | 2013/155365 A1 | 10/2013 |
| WO | 2015/160843 A1 | 10/2015 |
| WO | 2015160842 A1 | 10/2015 |
| WO | 2017/062665 A1 | 4/2017 |
| WO | 2018/136943 A1 | 7/2018 |

OTHER PUBLICATIONS

Bonnie K. McMillen, R.N., B.S.N. ("Home Remedy for Cough," College Health Nurse, University of Pittsburgh at Bradford, Bradford, PA. https://web.archive.org/web/20100301115138/http://www.pitt.edu/ ~cjm6/sp99cough.html: pp. 1-2. Mar. 1, 2010).

CureZone, Internet message board, http://www.curezone.org/forums/fm.asp?i=1519224#i, Ginger, cinnamon, turmeric, cayenne pepper and spirits posted Nov. 5, 2009.

Definition of Gel by Merriam-Webster. http://www.merriam-webster.com/dictionary/gel. Accessed Jan. 4, 2018. (Year 2018).

Demina et al. 2016. (Moscow, Russian Federation) vol. 65, Issue4, pp. 42-44, 2016, "Release of biologically active compounds of ginger (*Zingiber officinale* Roscoe.) extract from capsules" (Abstract only).

Ha et al Neuropharmocology, 2012, 63, 211-223 (Year: 2012).

Hoseinzadeh, et al. 2015. Med J Islam Repub Iran 2015; 29: 261, Published Sep. 12, 2015, "Acute effects of ginger extract on biochemical and functional symptoms of delayed onset muscle soreness."

International Search Report and Written Opinion for International Application No. PCT/US2015/025810 dated Jul. 1, 2015 (14 pages).

International Search Report and Written Opinion for International Application No. PCT/US2015/025811 dated Jul. 1, 2015.

International Search Report and Written Opinion for International Application No. PCT/US2016/055821 dated Dec. 30, 2016 (10 pages).

International Search Report for International Application No. PCT/US11/045480, dated Dec. 14, 2011 (3 pages).

J. Crow Company ("Cayenne Pepper." J. Crow Company, New Ipswich, NH. http://web.archive.org/web/20080202032007/http://www.jcrows.com/cayenne.html#prostate: p. 28 Feb. 2, 2008).

JIN + JA website: http://www.drinkjinja.com/pages/about-us, Mar. 31, 2013 (date as provided by the Internet Archive Wayback Machine, <http://archive.org/web>).

Jin, et al. 2014. Korean J Physiol Pharmacol; Apr. 2014;18(2) 149-53., "Ginger and its pungent constituents non-competitively inhibit serotonin currents on visceral afferent neurons."

Lakhan, et al. 2015. Nutr J 2015; 14:50. "Zingiberaceae extracts for pain: a systematic review and meta-analysis".

Ling et al. "6-Shogoal, an active constituent of ginger, inhibits breast cancer cell invasion by reducing matrix metalloproteinase-9 expression via blockade of nuclear factor-kB activation" British Journal of Pharmacology 2010, 161, 1763-1777.

Luo et al., "Targeting Pain-evoking Transient Receptor Potential Channels for the Treatment of Pain." Current Neuropharmacology 11: 652-663, 2013.

Maghbooli, et al. 2013. Phytother Res Mar. 2014; 28(3):412-5. "Comparison between the efficacy of ginger and Sumatriptan in the ablative treatment of the common migrane."

Miller, et al. 2010. Med Sci Sports Exerc. May 2010; 42(5):953-61. "Reflex inhibition of electrically induced muscle cramps in hypohydrated humans."

Montell, "New light on TRP and TRPL," Mol Pharmacol. 52:755-763 (1997).

Ofner, Reconstitutable Oral Suspensions, Chapter 6, pp. 243-258, in Pharmaceutical Dosage Forms. vol. 2: Disperse Systems, New York Marcel Dekker, Inc, 1996.

Opinion of the Scientific Committee on Food on Capsaicin (European Commission, Health & Consumer Protection Directorate General, Feb. 28, 2002).

Philips et al. Lancet Neurology, 2011, 10, 253-263 (Year: 2011).

Rowe et al., Eds., Handbook of Pharmaceutical Excipients, 6th Edition, Pharmaceutical Press (2009).

Search Report for Singapore Application No. 11201608383W issued by Intellectual Property Office of Singapore dated Nov. 29, 2017 (4 pages).

Supplementary European Search Report for European Application No. EP 11813088.9 dated Jun. 6, 2014.

Supplementary European Search Report for European Application No. EP15780197 dated Jan. 17, 2018.

Terry, et al. 2011. Pain Med Dec. 2011;12(12) 1808-18. "The use of ginger (*Zingiber officinale*) for the treatment of pain: a systematic review of clinical trials."

The George Mateljan Foundation (The World's Healthiest Foods: Visitors Questions. http://www.whfoods.com/genpage.php?tname=answeredquestion&dbid=130: pp. 1-3. Accessed Dec. 10, 2015).

Uthumpa, et al. 2013. Development of Nanoemulsion Formulations of Ginger Extract. Advanced Materials Research. 684. 12-15.

Vriens et al., "Herbal compounds and toxins modulating TRP channels," Curr Neuropharmacol. 6:79-96 (2008).

Written Opinion for International Application No. PCT/US11/45480, dated Dec. 14, 2011 (7 pages).

Written Opinion for International Application No. PCT/US2016/055821 dated Dec. 30, 2016 (7 pages).

U.S. Appl. No. 14/450,384, filed Aug. 4, 2014, Methods and Compositions for Preventing and Relieving Muscle Cramps and for Recovery from Neuromuscular Irritability and Fatigue Following Exercise, Issued as U.S. Pat. No. 9,937,135 on Apr. 10, 2018.

U.S. Appl. No. 15/241,986, filed Aug. 19, 2016, Methods of Treating Muscle Cramping and Related Compositions, Issued as U.S. Pat. No. 10,568,853 on Feb. 25, 2020.

U.S. Appl. No. 16/727,508, filed Dec. 26, 2019, Methods of Treating Muscle Cramping and Related Compositions, Pending.

U.S. Appl. No. 15/908,070, filed Feb. 28, 2018, Ion Channel Activators and Methods of Use, Pending.

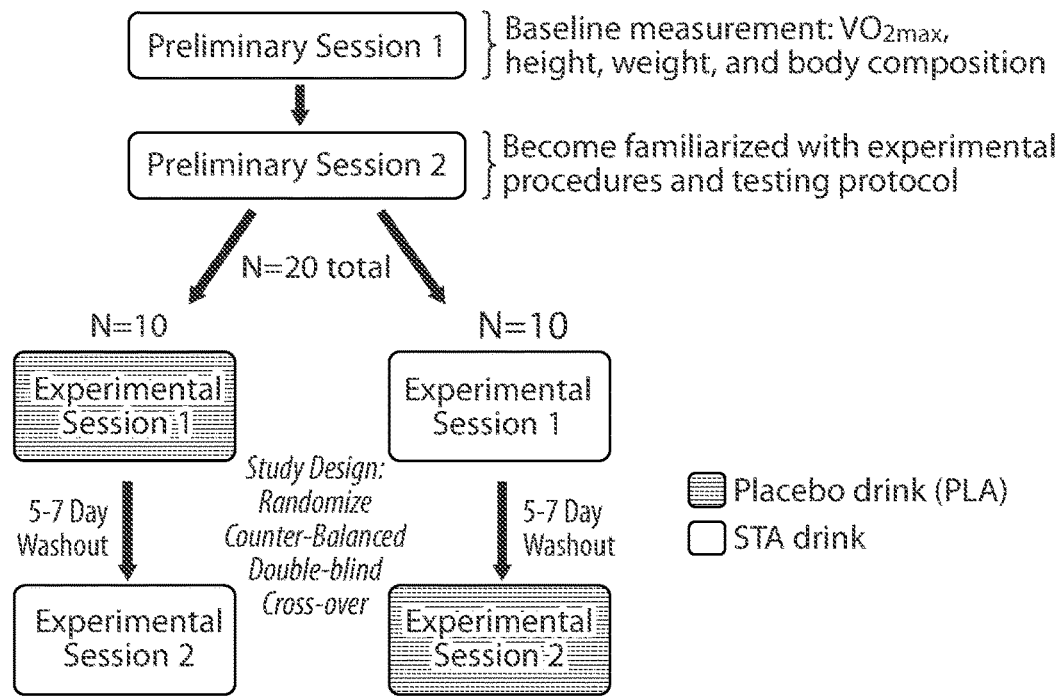
FIG. 1A
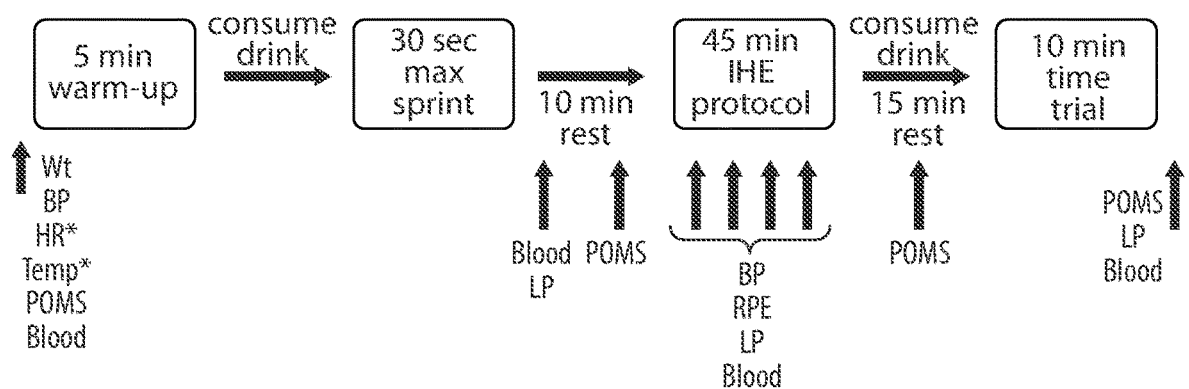
FIG. 1B
| | Age (years) | Height* (cm) | Weight* (kg) | Body Fat* (%) | VO2max* (ml/kg/min) | VO2max* (L/min) |
|---|---|---|---|---|---|---|
| Male (n=10) | 23.9±4.3 | 179.0±7.8 | 84.0±10.8 | 16.5±5.4 | 40.4±3.8 | 3.4±0.4 |
| Female (n=10) | 21.5±1.8 | 164.4±5.3 | 60.4±6.5 | 24.4±4.6 | 45.4±5.2 | 2.7±0.3 |
FIG. 2

COMPOSITIONS AND METHODS AFFECTING EXERCISE PERFORMANCE

CROSS-REFERENCE TO RELATED APPLICATIONS

This application is a U.S. National Phase Application under 35 U.S.C. § 371 of International Application No. PCT/US2018/014872, filed Jan. 23, 2018, titled COMPOSITIONS AND METHODS AFFECTING EXERCISE PERFORMANCE, which claims the benefit under 35 U.S.C. § 119(e) of U.S. Provisional Application No. 62/449,411, filed Jan. 23, 2017, titled COMPOSITIONS AND METHODS AFFECTING EXERCISE PERFORMANCE, both of which are hereby incorporated by reference in their entirety for all purposes.

BACKGROUND

Athletes often seek nutritional ergogenic aids to maintain optimal physical performance and mental function during exercise as well as to enhance recovery between bouts of exercise. As shown herein, compositions that include activators of TRP and ASIC channels may be useful to improve or preserve exercise performance and exercise recovery.

SUMMARY OF THE INVENTION

Described herein are compositions comprising activators of TRP and ASIC channels and methods of use thereof to improve or preserve exercise performance and exercise recovery. In one aspect, the present invention features a method of improving or preserving physical performance during exercise in a subject, wherein the method comprises orally administering to the subject a composition (e.g., a beverage) comprising a TRP channel activator and an excipient. In some embodiments, the TRP channel activator is selected from a capsaicinoid, a gingerol, or cinnamaldehyde.

In some embodiments, improving or preserving the physical performance comprises shortening the time to complete an exercise, e.g., a sprint or cycling exercise by the subject, e.g., relative to a reference standard. In some embodiments, improving or preserving the physical performance comprises an increase in the maximal oxygen consumption ($VO_2$ max) in the subject, e.g., relative to a reference standard. In some embodiments, improving or preserving the physical performance comprises a decrease in the fatigue of the subject, e.g., as measured by the Fatigue Index, e.g., relative to a reference standard. In some embodiments, improving or preserving the physical performance comprises exhibiting a greater mean power, total power, or interval power during a test (e.g., a sprint test, e.g., as described in Example 1). In some embodiments, improving or preserving the physical performance comprises improving the time trial distance of a subject (e.g., as described in Example 1). In some embodiments, improving or preserving the physical performance comprises increasing the energy (e.g., the mental energy), improving the mood, or reducing the exertion and pain (e.g., perceived exertion and pain) of a subject, e.g., relative to a reference standard.

In another aspect, the present invention features a method of improving or preserving recovery after exercise in a subject, wherein the method comprises orally administering to the subject a composition (e.g., a beverage) comprising a TRP channel activator and an excipient. In some embodiments, the TRP channel activator is selected from a capsaicinoid, a gingerol, or cinnamaldehyde. In some embodiments, improving or preserving recovery comprises reducing pain in a subject (e.g., reducing leg pain).

In another aspect, the present invention features a method of reducing inflammation in a subject, wherein the method comprises orally administering to the subject a composition (e.g., a beverage) comprising a TRP channel activator and an excipient. In some embodiments, the TRP channel activator is selected from a capsaicinoid, a gingerol, or cinnamaldehyde. In some embodiments, the inflammation occurs as a result of exercise.

In any and all embodiments, in some aspects, the TRP channel activator comprises a TRPA1 channel activator or a TRPV1 channel activator. In some embodiments, the capsaicinoid comprises capsaicin. In some embodiments, the composition comprises at least two of a capsaicinoid, a gingerol, or cinnamaldehyde and an excipient. In some embodiments, the composition comprises each of a capsaicinoid, a gingerol, or cinnamaldehyde and an excipient. In some embodiments, the amount of the TRP channel activator in the composition (e.g., beverage) is between about 0.001% to 1% weight/weight (w/w) of TRPA1 channel activator per weight of the composition (e.g., beverage).

In some embodiments, the excipient comprises a disintegrant, a binder, a surfactant, an emulsifier, a viscosity modifier, a lubricant, a sweetener, a pH-adjusting agent, a preservative, a flavoring agent, a coloring agent, or an antioxidant. In some embodiments, the excipient comprises an emulsifier, a sweetener, a pH-adjusting agent, a preservative, or a flavoring agent. In some embodiments, the excipient is selected from gellan gum, carob bean gum, locust bean gum, carrageenan, alginates, agar, guar gum, xanthan gum, carboxymethyl cellulose, clear starch, pectin, gelatin, cornstarch, katakuri starch, potato starch, and gum arabic. In some embodiments, the excipient comprises a sweetener selected from high fructose corn syrup, mannose, maltose, glucose polymers, sucrose, glucose, dextrose, lactose, galactose, fructose, polysaccharides, rice syrup, honey, saccharin, cyclamates, acetosulfam, sorbitol, sucralose, xylitol, erythritol, *Stevia* extract, L-aspartyl-L-phenyl-alanine ester, L-aspartyl-D-alanine alkyl amides, L-aspartyl-L-1-hydroxymethylalkaneamide, and L-aspartyl-1-hydroxyethylalkaneamide. In some embodiments, the excipient comprises a pH-adjusting agent selected from hydrochloric acid, citric acid, sodium hydrogen carbonate, potassium hydroxide, sodium hydroxide, and sodium carbonate. In some embodiments, the excipient comprises a preservative selected from sorbic acid, benzoic acid, sodium benzoate, sodium chloride, calcium benzoate, potassium benzoate, potassium sorbate, calcium sorbate, and sodium sorbate. In some embodiments, the excipient comprises a flavoring agent selected from almond oil, amaretto oil, anethole, anise oil, benzaldehyde, blackberry, black walnut oil, blueberry, caraway, caraway oil, cardamom oil, cardamom seed, cherry juice, cherry syrup, cinnamon, cinnamon oil, cinnamon water, citric acid, citric acid syrup, clove oil, cocoa, coriander oil, dextrose, eriodictyon, ethyl acetate, ethyl vanillin, fennel oil, ginger, glucose, glycerin, *glycyrrhiza*, grape, honey, lavender oil, lemon oil, lemon juice, lime, lime juice, mannitol, methyl salicylate, *myristica* oil, orange oil, orange peel, orange syrup, peppermint, peppermint oil, peppermint water, phenylethyl alcohol, pineapple, raspberry juice, raspberry syrup, rosemary oil, rose oil, rose water, sarsaparilla syrup, salt (e.g., sea salt), sorbitol, spearmint, spearmint oil, strawberry, sucrose, thyme oil, tolu balsam, vanilla, vanillin, and wild cherry syrup.

In some embodiments, the composition (e.g., beverage) is bottled or packaged in a unit that contains between 10 mL and 1000 mL of the composition (e.g., beverage). In some embodiments, the beverage is bottled or packaged in a unit that contains 50 mL or 100 mL of the beverage.

In some embodiments, the composition is administered to the subject prior to commencement of exercise (e.g., at least about 1 minute, about 2 minutes, about 5 minutes, about 10 minutes, about 15 minutes, about 20 minutes, about 30 minutes, about 45 minutes, about 1 hour, about 1.5 hours, about 2 hours, or more).

BRIEF DESCRIPTION OF DRAWINGS

FIGS. 1A-1B are figures outlining the overall study design (FIG. 1A) and the measurement timeline during experimental sessions 1 and 2 (FIG. 1B) as set forth in Example 1.

FIG. 2 is a table summarizing exemplary subject characteristics of the participants in the study outlined in Example 1.

DETAILED DESCRIPTION OF THE INVENTION

Figure 3A:
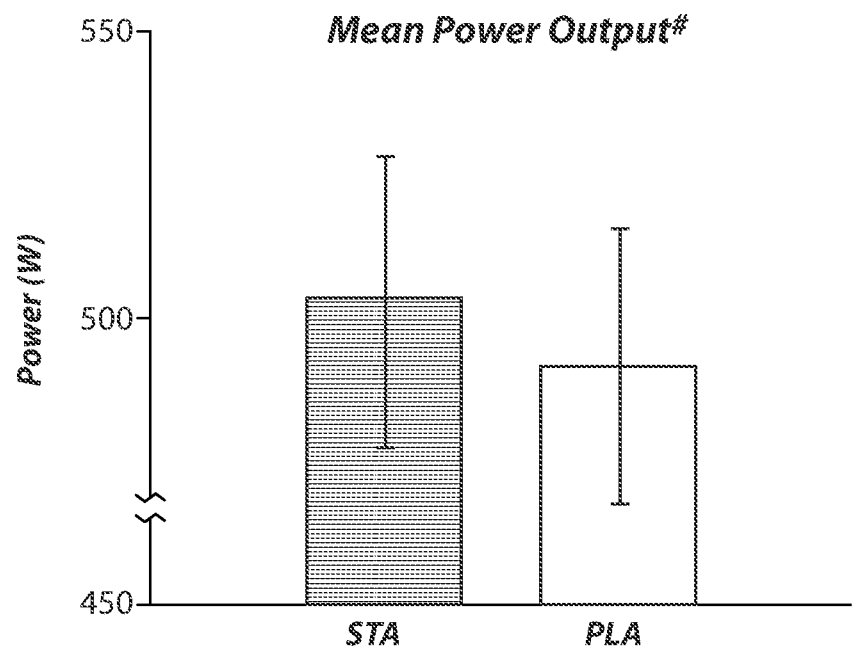
FIGS. 3A-3B are charts comparing the results of the 30-second maximal sprint in subjects that received either the experimental (STA) or vehicle (PLA) drink as mean power output (FIG. 3A) or total power output (FIG. 3B).
Figure 3B:
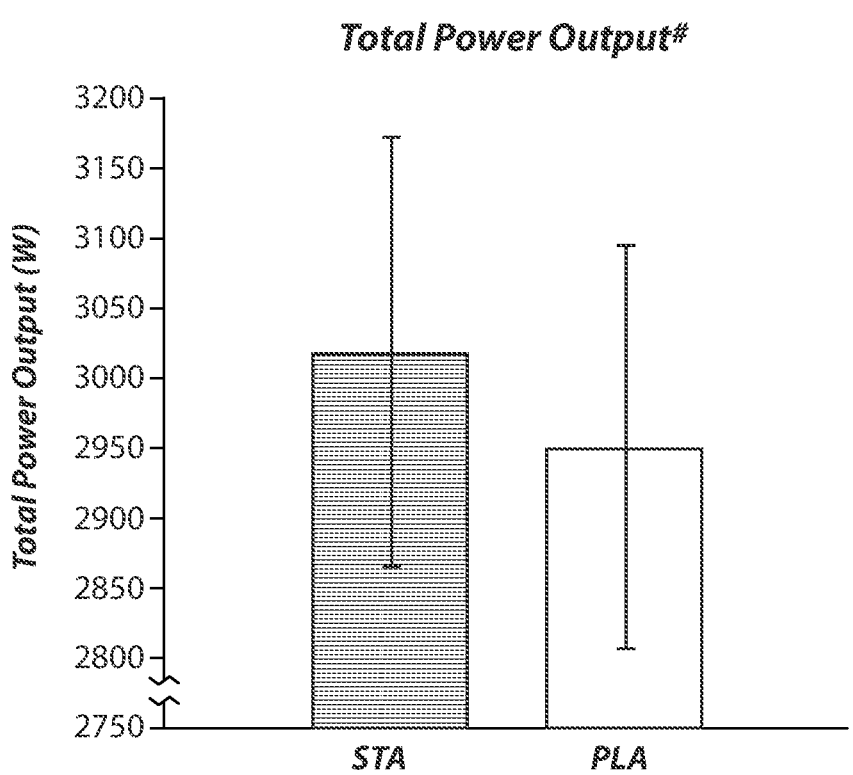
Figure 4:
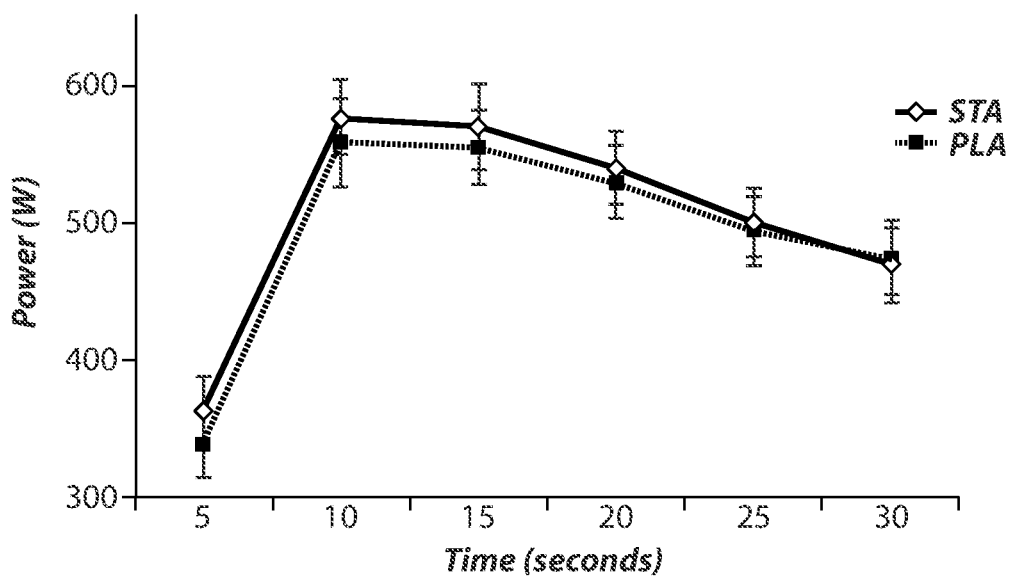
FIG. 4 is a graph comparing the results of the mean power during each 5-second interval of the 30-second maximal sprint in subjects that received either the experimental (STA) or vehicle (PLA) drink.
Figure 5:
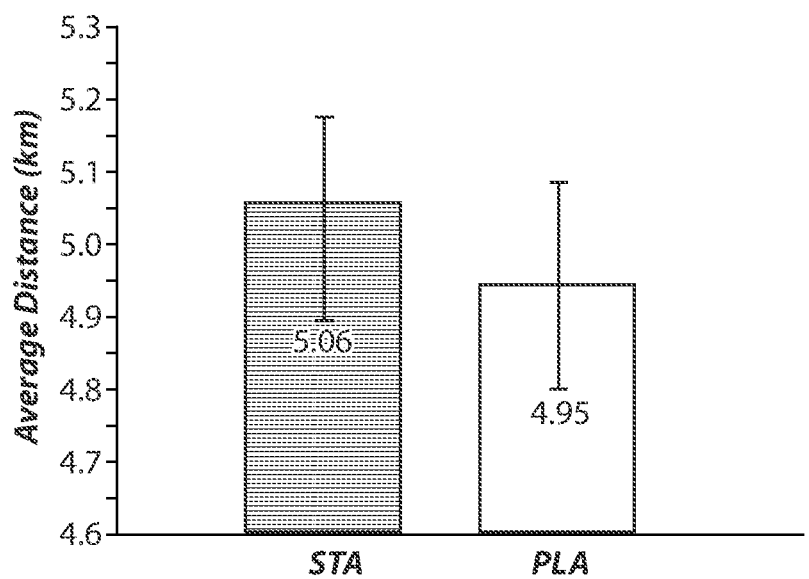
FIG. 5 is a chart comparing the results of the distance covered by subjects that received either the experimental (STA) or vehicle (PLA) drink in the 30-second maximal sprint.
Figure 6:
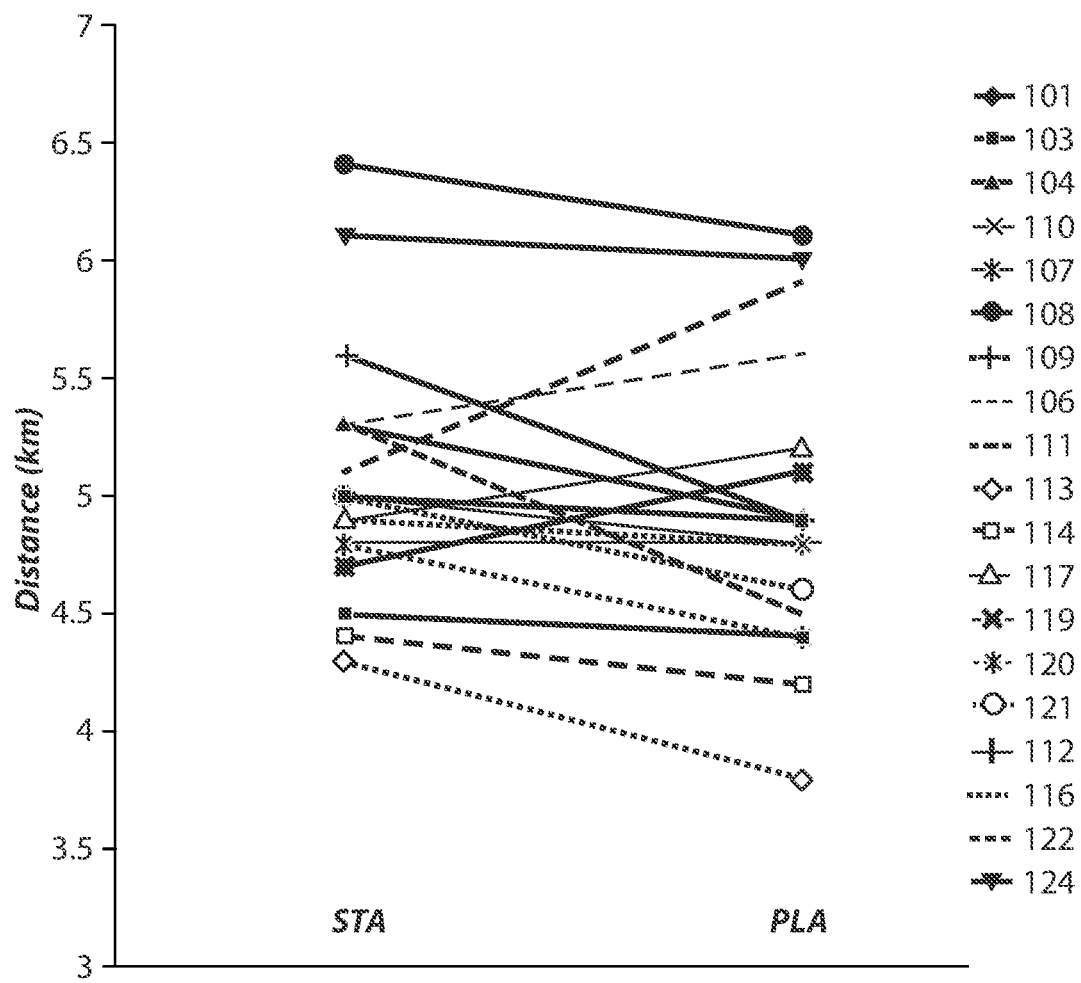
FIG. 6 is a graph showing the individual time trial distance by treatment for each subject in the study outlined in Example 1.

The methods and compositions of the present invention are directed to improving or preserving exercise performance and exercise recovery in a subject in need thereof. Exemplary compositions comprise a TRP channel activator or an ASIC channel activator formulated for oral consumption.

Definitions

The use of the words "a" or "an" when used in conjunction with the term "comprising" herein may mean "one," but are also consistent with the meaning of "one or more," "at least one," and "one or more than one."

The term "acidulant" as used herein refers to an acidic compound (e.g., an acid) used to lower the pH of a composition. In some embodiments, the pH can be lowered in the range of about 2.5 to about 6.5 (e.g., pH of 2.5, 3.0, 3.5, 4.0, 4.5, 5.0, 5.5, 6.0, or 6.5). In some embodiments, the pH can be lowered in the range of about 1.5 to about 5.0 (e.g., pH of 1.5, 2.0, 2.5, 3.0, 3.5, 4.0, 4.5, 5.0), for example, in the range of about 1.5 to about 4.4 (e.g., pH of 1.5, 2.0, 2.5, 3.0, 3.5, 4.0, 4.4).

"Acquire" or "acquiring" as the terms are used herein, refer to obtaining possession of a value, e.g., a numerical value, or image, or a physical entity (e.g., a sample), by "directly acquiring" or "indirectly acquiring" the value or physical entity. "Directly acquiring" means performing a process (e.g., applying or measuring a current to or from a subject, or capturing a signal from a subject or sample or performing a synthetic or analytical method) to obtain the value or physical entity. "Indirectly acquiring" refers to receiving the value or physical entity from another party or source (e.g., a third party laboratory that directly acquired the physical entity or value). Directly acquiring a value or physical entity includes performing a process that includes a physical change in a physical substance or the use of a machine or device.

The term "agonist," as used herein, refers to a molecule that stimulates a biological response. In some embodiments, an agonist is an activator. In some embodiments, the agonists and activators referred to herein may activate a TRP ion channel (e.g., TRPV1 or TRPA1) or an ASIC ion channel.

The term "administering" and "administration" refers to a mode of delivery. A daily dosage can be divided into one, two, three or more doses in a suitable form to be administered one, two, three or more times throughout a time period. In preferred embodiments of the present invention, compositions and solutions are administered orally.

The terms "analog" or "related analogs" as used herein in regard to a compound or compounds refer to a substance that has a similar chemical structure to another compound, but differs from it with respect to a certain component or components.

The term "derivative" as used herein refers to a substance produced from another substance either directly or by modification or partial substitution.

"Muscle cramp" as used herein is a muscle cramp which is treated with the composition described herein. In some embodiments, it is not induced but rather arises spontaneously either from activity or underlying disease etiology, e.g., exercise. In some embodiments, the muscle cramp can be a contraction of a skeletal muscle or the smooth muscle. In some embodiments, the muscle cramp is a contraction of a skeletal muscle, e.g., the flexor hallucis *brevis* muscle.

As used herein, the terms "prevent" or "preventing" as used in the context of a disorder or disease, refer to administration of an agent to a subject such that the onset of at least one symptom of the disorder or disease is delayed as compared to what would be seen in the absence of administration of said agent. As compared with an equivalent untreated control, such prevention is at least 5%, 10%, 20%, 30%, 40%, 50%, 60%, 70%, 80%, 90%, 95%, 99%, or 100%, as measured by any standard technique.

The term "subject" as used herein refers to a mammal, including, but not limited to, a human or non-human mammal, such as a bovine, equine, canine, ovine, or feline mammal. In some embodiments, the term subject refers to a human (e.g., a human male or female).

As used herein, the term "substantially pure" refers to a composition that is free of organic and/or inorganic species that do not activate the TRPV1, TRPA1, or/or ASIC channels, and where 60%, 65%, 70%, 75%, 80%, 85%, 90%, 95%, 97%, 98%, 99%, or 99.5% (w/w) of the composition is comprised of a single chemical species. Substantially pure compositions can be prepared and analyzed using standard methods known in the art (e.g., chromatographic separation, extractions, and the like). In some embodiments, substantially pure compositions do not include isomeric impurities (e.g., geometric isomers) and/or salts or solvates of a particular chemical species.

"Treat" or "treating" as used herein refers to administering a composition for therapeutic purposes or administering treatment to a subject to improve at least one symptom of already suffering from a disorder to improve the subject's condition. By "treating a condition or disorder" or "alleviating a condition or disorder" is meant that the condition or disorder and the symptoms associated with the condition or disorder are, e.g., prevented, alleviated, reduced, cured, or placed in a state of remission. As compared with an equivalent untreated control, such alleviation or degree of treatment is at least 5%, 10%, 20%, 30%, 40%, 50%, 60%, 70%, 80%, 90%, 95%, 99%, or 100%, as measured by any standard technique.

The term "viscosity" as used herein refers to a measurement of a fluid's internal resistance to flow (e.g., "thickness"). Viscosity is generally expressed in centipoise (cP) or pascal-seconds.

Other features and advantages of the invention will be apparent from the Detailed Description, Examples, and Claims.

Products and Compositions

The compositions described herein are suitable for oral consumption by a subject (e.g., by a human) and include an activator of a TRP channel (e.g., TRPV1, TRPA1) or an activator of an ASIC channel, as well as one or more optional excipients as described herein. Exemplary, non-limiting compositions include those that are solids (e.g., chews or chewing gums), liquids (e.g., beverages), and gels.

TRPV1 Channel Activators

Compounds that activate TRPV1 that may be used in the compositions of the present invention include, for example, capsaicin, capsaicin analogs and derivatives (e.g., capsaicinoids), and any other compound that activates TRPV1, examples of which are described herein. Modulators of TRPV1 activity are known in the art (see, e.g., Harteneck et al., *Adv Exp Med Biol.* 704:87-106, 2011, and other references described herein).

In one embodiment, the TRPV1 channel activator is a capsaicinoid (e.g., capsaicin (8-methyl-N-vanillyl-trans-6-nonenamide)). Exemplary capsaicinoids are provided in Table 1.

TABLE 1

Exemplary capsaicinoids

| | |
|---|---|
| Capsaicin | 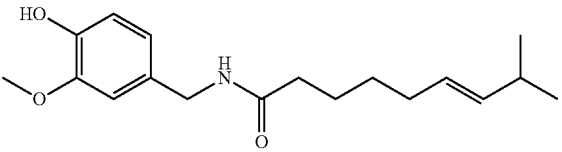 [SMILES: COc1cc(CNC(=O)CCCC/C=C/C(C)C)ccc1O] |
| Dihydrocapsaicin | 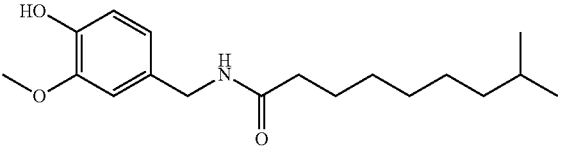 [SMILES: COc1cc(CNC(=O)CCCCCCC(C)C)ccc1O] |
| Nordihydrocapsaicin | 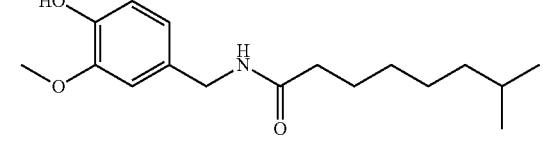 |
| Homodihydrocapsaicin | 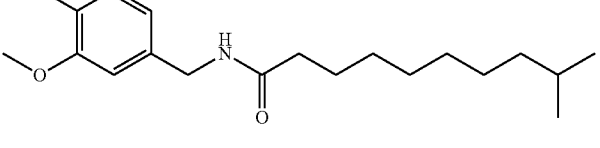 |
| Homocapsaicin | 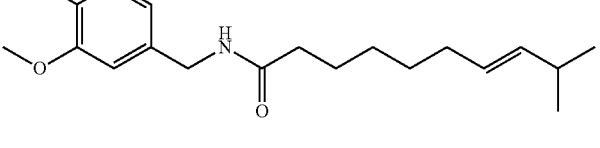 |
| Nonivamide | 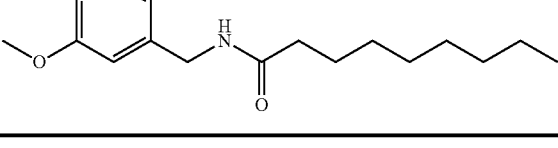 |

Suitable capsaicinoids and capsaicinoid analogs and derivatives for use in the compositions and methods of the present invention include naturally occurring and synthetic capsaicin derivatives and analogs including, e.g., vanilloids (e.g., N-vanillyl-alkanedienamides, N-vanillyl-alkanedienyls, and N-vanillyl-cis-monounsaturated alkenamides), capsiate, dihydrocapsiate, nordihydrocapsiate and other capsinoids, capsiconiate, dihydrocapsiconiate and other coniferyl esters, capsiconinoid, resiniferatoxin, tinyatoxin, civamide, N-phenylmethylalkenamide capsaicin derivatives, olvanil, N-[(4-(2-aminoethoxy)-3-methoxyphenyl) methyl]-9Z-octa-decanamide, N-oleyl-homovanillamide, triprenyl phenols (e.g., scutigeral), gingerols, piperines, shogaols, guaiacol, eugenol, zingerone, nuvanil, NE-19550, NE-21610, and NE-28345.

Other suitable TRPV1 channel activators include oleoylethanolamide, N-oleoyldopamine, 3-methyl-N-oleoyldopamine, oleamide, capsiate, 1-monoacylglycerols having C18 and C20 unsaturated and C8-C12 saturated fatty acid, 2-monoacylglycerols having C18 and C20 unsaturated fatty acids, miogadial, miogatrial, polygodial, and other terpenoids with an alpha,beta-unsaturated 1,4-dialdehyde moiety, sanshools, evodiamine, acesulfame-K, cyclamate, sulfates (e.g., $CuSO_4$, $ZnSO_4$, and $FeSO_4$), arvanil, anandamide, N-arachidonoyl-dopamine, flufenamic acid dopamide and other dopamine amides of fenamic acids, 4-hydroxynonenal, SA13353 (i.e., 1-[2-(1-adamantyl)ethyl]-1-pentyl-3-[3-(4-pyridyl)propyl]urea), gingerol or salts of magnesium.

In addition, the TRPV1 channel activator may be an analog or derivative of any of the TRPV1 channel activators described herein.

Additional TRPV1 channel activators are described, for example, in U.S. Pat. Nos. 7,632,519; 7,446,226; 7,429,673; 7,407,950; 6,022,718; 5,962,532; 5,762,963; 5,403,868; 5,290,816; 5,221,692; 4,812,446; 4,599,342; 4,564,633; 4,544,669; 4,544,668; 4,532,139; 4,493,848; 4,424,205; 4,313,958; in U.S. Patent Application Publication Nos. 2007/0293703; 2007/0167524; 2006/0240097; and 2005/0085652; and in WO 00/50387, each of which is incorporated by reference.

In addition, the TRPV1 channel activator may be an acidulant (e.g., acetic acid, phosphoric acid, citric acid, malic acid, succinic acid, tartaric acid, fumaric acid, or ascorbic acid) maintaining a low pH in the range of 2.5-6.5 (e.g., pH of 2.5, 3.0, 3.5, 4.0, 4.5, 5.0, 5.5, 6.0, or 6.5).

TRPV1 channel activators for use in the compositions and methods described herein can be identified using standard methodology, as described, for example, in U.S. Patent Application Publication No. 2003/0104085, which is hereby incorporated by reference. Exemplary assays for identification of TRPV1 channel activators include, without limitation, receptor binding assays; functional assessments of stimulation of calcium influx or membrane potential in cells expressing the TRPV1 receptor; assays for the ability to induce cell death in such cells (e.g., selective ablation of C-fiber neurons); and other assays known in the art.

A TRPV1 channel activator may be present in a composition of the invention at a concentration range of about 0.001% to about 50% weight by weight (w/w) based on the total weight or total volume of the composition (e.g., 0.005%, 0.01%, 0.05%, 0.01%, 0.1%, 0.5%, 1%, 2%, 3%, 4%, 5%, 10%, 15%, 20%, 30%, 40% or 50%). In some embodiments, a TRPV1 channel activator is present between 0.001% to 1% weight/weight (w/w) per weight of the composition. In some embodiments, a composition described herein comprises between about 0.0001 to about 0.1 mg TRPV1 channel activator (e.g., about 0.0001 to about 0.01 mg, or about 0.001 mg to about 0.01 mg, or about 0.01 mg to about 0.1 mg TRPV1 channel activator per mL or mg of composition.

TRPA1 Channel Activators

TRPA1 channels are activated by naturally occurring substances including, e.g., mustard oil, isothiocyanate compounds (e.g., allyl isothiocyanate), acrolein, farnesyl thiosalicylic acid, $\Delta_9$-tetrahydrocannabinol (THC), eugenol, ginger, gingerol, gingerols, shogaols, nicotine, nicotine derivatives and analogs, methyl salicylate, cinnamaldehyde, cinnamon oil, wintergreen oil, clove oil, allicin, diallyl sulfide, diallyl disulfide, diallyl trisulfide, sanshools, farnesyl thiosalicylic acid, and farnesyl thioacetic acid. The TRPA1 channel activator may also be an analog or derivative of any of the TRPA1 channel activators described herein, and additional TRPA1 channel activators are identified in WO 2009/071631, hereby incorporated by reference. Still other modulators of TRPA1 are described in, e.g., Harteneck et al., "Synthetic modulators of TRP channel activity," Adv Exp Med Biol. 704:87-106, 2011; Viana et al. "TRPA1 modulators in preclinical development," Expert Opin. Ther. Pat. 19(12):1787-99, 2009).

Methods for identifying TRPA1 channel activators are known in the art and are described, for example, in U.S. Pat. No. 7,674,594.

A TRPA1 channel activator may be present in a composition of the invention at a concentration range of about 0.001% to about 50% weight by weight (w/w) based on the total weight or total volume of the composition (e.g., 0.005%, 0.01%, 0.05%, 0.01%, 0.1%, 0.5%, 1%, 2%, 3%, 4%, 5%, 10%, 15%, 20%, 30%, 40% or 50%). In some embodiments, a TRPA1 channel activator is present between 0.001% to 1% weight/weight (w/w) per weight of the composition. In some embodiments, a composition described herein comprises between about 0.0001 to about 0.1 mg TRPA1 channel activator (e.g., about 0.0001 to about 0.01 mg, or about 0.001 mg to about 0.01 mg, or about 0.01 mg to about 0.1 mg TRPA1 channel activator per mL or mg of composition.

ASIC Channel Activators

ASIC channels are activated by low pH. The pH of a composition of the present invention that includes an ASIC channel activator may be in the range of 2.5-6.5 (e.g., pH of 2.5, 3.0, 3.5, 4.0, 4.5, 5.0, 5.5, 6.0, or 6.5). The pH may be adjusted within this range by any means acceptable for compositions that are intended to be ingested by a subject. Exemplary acidulants are acetic acid, phosphoric acid, citric acid, malic acid, succinic acid, tartaric acid, fumaric acid, and ascorbic acid. The ASIC channel activator may be present in a composition of the invention at a concentration range of about 0.001% to about 50% weight by weight (w/w) based on the total weight or total volume of the composition (e.g., 0.005%, 0.01%, 0.05%, 0.01%, 0.1%, 0.5%, 1%, 2%, 3%, 4%, 5%, 10%, 15%, 20%, 30%, 40% or 50%). In some embodiments, an ASIC channel activator is present between 0.001% to 1% weight/weight (w/w) per weight of the composition. In some embodiments, a composition described herein comprises between about 0.0001 to about 0.1 mg an ASIC channel activator (e.g., about 0.0001 to about 0.01 mg, or about 0.001 mg to about 0.01 mg, or about 0.01 mg to about 0.1 mg an ASIC channel activator per mL or mg of composition.

Additional Components of the Composition

The composition of the present invention comprises a TRP channel activator or an ASIC channel activator and an excipient. Exemplary excipient include electrolytes (e.g., potassium salt or other salts), buffering agents, sweeteners, flavoring and coloring agents, vitamins, minerals, preservatives, viscosity modifiers, thickening agents, dissolving agents, solvents, and antioxidants as described below. Other exemplary excipients are described in *Handbook of Pharmaceutical Excipients*, 6$^{th}$ Edition, Rowe et al., Eds., Pharmaceutical Press (2009).

Viscosity Modifiers and Thickening Agents

Viscosity is the ratio of shear stress to shear rate, expressed as dynes-second/cm$^2$, or poise. A centipoise (cP) is one one-hundredth of a poise.

The composition of the present invention may have a viscosity greater than water (i.e., about 1.0 cP at 20° C.), e.g., about 100, 200, 300, 400, 500, 1000, 1500, 2000, 2500, 3000, 3500, 4000, 4500, 5000, 6000, 7000, 8000, 9000 cP or more. If a consistency of corn syrup is desired, viscosities in the range of about 2500 cP are suitable. If a consistency of a soft gel or honey is desired, viscosities in the range of about 10000 cP to about 15000 cP are suitable. For pudding-like products, viscosities in the range of about 30000 cP to about 38000 cP are desirable. Viscosity of the compositions of the present invention may be measured with, e.g., a rheometer or viscometer, though additional methods of measuring viscosity are known in the art.

Viscosity modifiers and thickening agents may be added to compositions of the present invention. Such viscosity modifiers and thickening agents include, for example, collagen, gellan gum, carbohydrate gel-forming polymers, carob bean gum, locust bean gum, carrageenan, alginates (e.g., alginic acid, sodium alginate, potassium alginate, ammonium alginate, and calcium alginate), agar, guar gum, xanthan gum, microcrystalline cellulose, carboxymethyl cellulose, ethyl cellulose, clear starch, pectin, gelatin, arrowroot, cornstarch, katakuri starch, potato starch, sago, tapioca, furcellaran, karo syrup (e.g., light karo syrup and dark karo syrup), glycerin, and sodium pyrophosphate. A viscosity modifier or thickening agent may be present in the composition in an amount of from about 0.01% to about 10% by weight based on the total weight or volume of the composition (e.g., about 0.01, about 0.1, about 0.5, about 1, about 2%, about 3%, about 4%, about 5%, about 6%, about 7%, about 8%, about 9%, or about 10%), though the viscosity modifier or thickening agent may be present in lower or higher concentrations (e.g., about 10%, about 20%, about 30%, about 40%, about 50%, about 60%, about 70%, about 80%, or about 90%). In some embodiments, the viscosity modifier or thickening agent is present in the composition from about 40% to about 60% (e.g, about 50%).

Electrolytes and Buffering Agents

Exemplary electrolytes and buffering agents include potassium salts, chloride salts, bromide salts, sodium salts, magnesium salts, calcium salts, citrate salts, acetate salts, phosphate salts, salicylates, bicarbonate salts (e.g., sodium bicarbonate), lactate salts, sulphate salts, tartrate salts, benzoate salts, selenite salts, molybdate salts, iodide salts, oxides, and combinations thereof. An electrolyte or buffering agent may be present in a composition of the invention at a concentration range of about 0.01% to about 10% by weight based on the total weight or volume of the composition (e.g., about 0.01%, about 0.02%, about 0.03%, about 0.04%, about 0.05%, about 0.1%, about 0.5%, about 1%, about 2%, about 3%, about 4%, about 5%, about 6%, about 7%, about 8%, about 9%, or about 10%), though an electrolyte or buffering agent may be present in lower or higher concentrations.

In certain embodiments, the compositions of the present invention include high concentrations of potassium (e.g., potassium chloride). The concentration of potassium in the composition may be, e.g., about 0.01%, about 0.02%, about 0.03%, about 0.04%, about 0.05%, about 0.1%, about 0.5%, about 1%, about 2%, about 3%, about 4%, about 5%, about 6%, or about 7% or more by weight based on the total weight or volume of the composition.

In certain embodiments, the compositions of the present invention include high concentrations of magnesium (e.g., magnesium chloride). The concentration of magnesium in the composition may be, e.g., about 0.01%, about 0.02%, about 0.03%, about 0.04%, about 0.05%, about 0.1%, about 0.5%, about 1%, about 2%, about 3%, about 4%, about 5%, about 6%, or about 7% or more by weight based on the total weight or volume of the composition.

In some embodiments, an electrolyte or buffering agent may be added to the compositions of the present invention to affect the pH level. In some embodiments, the pH of the composition, e.g., with the addition of an electrolyte or buffering agent, is e.g., about 1.5, about 2.0, about 2.5, about 3.0, about 3.5, about 4.0, about 4.5, about 5.0, about 5.5, about 6.0, about 6.5, about 7.0, about 7.5, about 8.0, or about 8.5.

Sweeteners

Sweeteners may be included in the compositions of the invention. Exemplary sweeteners include corn syrup (e.g., high fructose corn syrup or karo syrup), mannose, maltose, glucose polymers, sucrose (e.g., cane sugar or beet sugar), glucose, dextrose, lactose, galactose, fructose, polysaccharides (e.g., malodextrins), rice syrup, honey, and natural fruit juices (e.g., orange juice, *papaya* juice, pineapple juice, apple juice, grape juice, apricot juice, pear juice, tomato juice, agave nectar, or cranberry juice). Additionally, non- or low-caloric sweeteners can be used in the compositions of the invention. Examples of such non-caloric or low-caloric sweeteners include, but are not limited to, saccharin, sodium saccharin, cyclamates, acetosulfam, sorbitol, mannitol, sucralose, xylitol, erythritol, *Stevia* extract, L-aspartyl-L-phenyl-alanine ester (e.g., aspartame), L-aspartyl-D-alanine alkyl amides, L-aspartyl-L-1-hydroxymethylalkaneamide, and L-aspartyl-1-hydroxyethylalkaneamide. In some embodiments, sweeteners may be present in a composition of the invention at a concentration range of about 2% to about 20% by weight based on the total weight or volume of the composition (e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20%), though sweeteners may be present in lower or higher concentrations.

Flavoring and Coloring Agents

Exemplary flavors and flavoring agents include almond oil, amaretto oil, anethole, anise oil, apple, benzaldehyde, blackberry, black walnut oil, blueberry, caraway, caraway oil, cardamom oil, cardamom seed, cherry juice, cherry syrup, chocolate, cinnamon, cinnamon oil, cinnamon water, citric acid, citric acid syrup, clove oil, cocoa, coriander oil, dextrose, eriodictyon, ethyl acetate, ethyl vanillin, fennel oil, ginger, glucose, glycerin, *glycyrrhiza*, grape, honey, lavender oil, lemon oil, lime, mannitol, methyl salicylate, mint (e.g., peppermint, spearmint), *myristica* oil, orange oil, orange peel, orange syrup, peppermint, peppermint oil, peppermint water, phenylethyl alcohol, pineapple, raspberry juice, raspberry syrup, rosemary oil, rose oil, rose water, sarsaparilla syrup, sorbitol, spearmint oil, strawberry, sucrose, thyme oil, tolu balsam, vanilla, vanillin, watermelon, and wild cherry syrup. Additional flavoring agents may be found in Food Chemicals Codex and Fenaroli's Handbook of Flavor Ingredients. Flavoring agents may be present in a composition of the invention at a concentration range of about 0.01% to about 20% by weight based on the total weight or volume of the composition (e.g., about 0.05%, about 0.1%, about 0.5%, about 1%, about 2%, about 3%, about 4%, about 5%, about 7.5%, about 10%, about 12.5%, about 15%, about 17.5%, or about 20%), though flavoring agents may be present in lower or higher concentrations.

Small amounts of a coloring agent may be utilized in the compositions of the present invention. Coloring agents include, e.g., beta-carotene, riboflavin dyes, FD&C dyes (e.g., Yellow No. 1, Blue No. 1, Blue No. 2, and Red No. 40), FD&C lakes, chlorophylls and chlorophyllins, caramel coloring, annatto, cochineal, turmeric, saffron, paprika, and fruit, vegetable, and/or plant extracts (e.g., grape, black currant, *aronia*, carrot, beetroot, red cabbage, elderberry, and hibiscus extracts). The amount of coloring agent used will vary depending on the agents used in the composition and the color intensity desired in the finished product. Coloring agents may be present in a composition of the invention at a concentration range of about 0.01% to about 20% by weight based on the total weight or volume of the composition (e.g., about 0.05%, about 0.1%, about 0.5%, about 1%, about 2%, about 3%, about 4%, about 5%, about 7.5%, about 10%, about 12.5%, about 15%, about 17.5%, or about 20%), though coloring agents may be present in lower or higher concentrations.

Vitamins and Minerals

Non-limiting examples of vitamins and minerals that may be included in the compositions of the present invention include, e.g., choline bitartrate, niacinamide, thiamin, folic acid, d-calcium pantothenate, biotin, vitamin A, vitamin C, vitamin $B_1$ hydrochloride, vitamin $B_2$, vitamin $B_3$, vitamin $B_6$ hydrochloride, vitamin $B_{12}$, vitamin D, vitamin E acetate, vitamin K, and salts of calcium, potassium, magnesium, zinc, iodine, iron, and copper. In some embodiments, vitamins and minerals may be present in a composition of the invention at a concentration range of about 0.01% to about 50% by weight based on the total weight or volume of the composition (e.g., about 0.05%, about 0.1%, about 0.5%, about 1%, about 2%, about 3%, about 4%, about 5%, about 7.5%, about 10%, about 12.5%, about 15%, about 17.5%, about 20%, about 25%, about 30%, about 35%, about 40%, about 45%, or about 50%), though vitamins and minerals may be present in lower or higher concentrations. In some embodiments, when included in a composition of the invention, the composition may contain at least about 5%, about 10%, about 15%, about 20%, about 25%, about 30%, about 35%, about 40%, about 45%, or about 50% of the U.S. recommended daily intake (RDI) for such vitamins and minerals.

Preservatives

A preservative may additionally be utilized in the compositions described herein. Exemplary preservatives include, for example, sorbate, polysorbate (e.g., polysorbate 20, polysorbate 40, polysorbate 80), a paraben (e.g., methylparaben sodium, propylparaben sodium), benzoate, and polyphosphate preservatives (e.g., sorbic acid, benzoic acid, calcium sorbate, sodium sorbate, potassium sorbate, calcium benzoate, sodium benzoate, potassium benzoate, and mixtures thereof). In some embodiments, the preservative may be present in a composition of the invention at a concentration range of about 0.0005% to about 0.5% (e.g., about 0.0005%, about 0.001%, about 0.005%, about 0.01%, about 0.05%, about 0.1%, or about 0.5%) by weight based on the total weight or volume of the composition, though preservatives may be present in lower or higher concentrations.

In some embodiments, a preservative may be added to the compositions of the present invention to affect the pH. In some embodiments, the pH of the composition, e.g., with the addition of a preservative, is e.g., about 1.5, about 2.0, about 2.5, about 3.0, about 3.5, about 4.0, about 4.5, about 5.0, about 5.5, about 6.0, about 6.5, about 7.0, about 7.5, about 8.0, or about 8.5. In some embodiments, the pH of the composition, e.g., with the addition of a preservative, is within the range of about 1.5 to about 7.5, about 1.75 to about 7.0, about 2.0 to about 6.5, about 2.1 to about 6.0, about 2.2 to about 5.5, about 2.3 to about 5.0, about 2.4 to about 4.5, about 2.5 to about 4.0, about 2.6 to about 3.5. In some embodiments, the pH of the composition, e.g., with the addition of a preservative, is within the range of about 1.5 to about 4.0.

Antioxidants

An antioxidant agent may also be included in the compositions to, for example, reduce exercise-induced oxidative stress. Exemplary antioxidants include vitamin C and vitamin E; beta-carotene, lutein, or other carotenoids; cyanidin, delphinidin, malvidin, or other anthocyanidins; apigenin, luteolin, or other flavones; hesperitin, naringenin, or other flavonones; isorhamnetin, quercetin, kaempferol or other flavonols; butylated hydroxyanisole and butylated hydroxytoluene; and epigallocatechin-3-gallate, epicatechin, thearubigins, or other flavan-3-ols. In some embodiments, an antioxidant may be present in a composition of the invention at a concentration range of about 0.0005% to about 0.5% (e.g., about 0.0005%, about 0.001%, about 0.005%, about 0.01%, about 0.05%, about 0.1%, or about 0.5%) by weight based on the total weight or volume of the composition, though antioxidants may be present in lower or higher concentrations.

Dissolving Agent or Solvent

A dissolving agent or solvent may also be included in the compositions to, for example, improve the suspension or emulsification of particular components. In addition, certain dissolving agents or solvents may have a preservative function. Exemplary dissolving agents or solvents include acetic acid, acetone, butanol, dimethyl sulfoxide, ethanol, ethyl acetate, isopropanol, methanol, petroleum ether and the like. In some embodiments, a dissolving agent or solvent may be present in a composition of the invention at a concentration range of about 0.0005% to about 0.5% (e.g., about 0.0005%, about 0.001%, about 0.005%, about 0.01%, about 0.05%, about 0.1%, or about 0.5%) by weight based on the total weight or volume of the composition, though dissolving agents or solvents may be present in lower or higher concentrations.

Additional components of the compositions described herein may include amino acids (e.g., leucine, isoleucine, lysine, methionine, phenylalanine, threonine, tryptophan, and valine), stimulants (e.g., caffeine), emulsifying agents, carbon dioxide (e.g., to carbonate a liquid composition), stabilizers, humectants, anticaking agents, or herbal extracts. These components may be included at levels from about 0.0005% to about 25% (e.g., about 0.0005%, about 0.001%, about 0.005%, about 0.01%, about 0.05%, about 0.1%, about 0.5%, about 1%, about 5%, about 10%, about 15%, about 20%, or about 25%) by weight based on the total volume of the composition, though an additional component may be present in lower or higher concentrations.

Combination Therapies

In certain embodiments, an additional therapeutic agent may be administered with compositions of the present invention, e.g., to improve or preserve exercise performance or exercise recovery. When combination therapy is employed, the additional therapeutic agent can be administered as a separate formulation or may be combined with any of the compositions described herein. For example, an additional therapeutic agent may be administered to improve or preserve exercise performance, prevent or treat muscle cramps, muscle soreness, or pain, or enhance mood. Such therapeutic agents include, for example, muscle relaxants (e.g., diazepam), anti-inflammatory agents (e.g., ibuprofen), steroids, hormones, diuretics, nutritional supplements (e.g., creatine), vitamins, stimulants (e.g., caffeine, amphetamines), and anti-depressants.

Formulations and Methods of Preparing Compositions

The compositions and solutions of the present invention may be formulated as ready-to-drink beverages, concentrates (e.g., syrups), dry compositions (e.g., powders, granules, or tablets that may be reconstituted with a liquid (e.g., with water), gels, solids, semi-solids (e.g., ice cream, pudding, or yogurt), frozen liquids (e.g., ice pops), lozenges or hard candies, dissolving strips (e.g., an edible strip containing pullulan and compositions of the invention), and chewing gum.

In some embodiments, the compositions may be in the form of a dry powder, granule, or tablet that may be reconstituted in a specified amount of a liquid. The dried components may be mixed together and milled (e.g., to create a homogenous powder) or mixed in aqueous solution and dried by using methods known to one of skill in the art. Dried powders or granules may be "loose" or fashioned into tablets.

The compositions described herein can be ingested, for example, by a subject before, during, or after exercise. In addition, the compositions and solutions described herein can be ingested (e.g., through eating or drinking) before the onset of muscle cramping, when muscle cramping begins, any time after the onset of muscle cramping, or after muscle cramping has subsided. The compositions of the solution can also be ingested after exercise to accelerate nerve-muscle recovery from exercise fatigue, or to reduce inflammation. When the compositions and solutions of the present invention are in the form of a ready-to-drink beverage, e.g., 1, 2, 4, 8, 10, 12, 14, 16, 18, 20, 24, 26, 28, 30, or 32 ounces of the beverage may be consumed as needed (e.g., once, twice, three, four, five, six times per day; once per week; or once per month).

The compositions and solutions of the present invention may be prepared using methods known to one of skill in the art. Such methods include dissolving, dispersing, or otherwise mixing all components singularly or in suitable combinations and agitating with, for example, a mechanical stirrer until all of the ingredients have been solubilized or adequately dispersed. Where a shelf-stable composition or solution is desired, the final mixture can be pasteurized, ultra-pasteurized, sterilized, or filled aseptically at appropriate process conditions. Where required for mutual stability of two or more components (for example if a component is unstable at low pH), multiple components can be mixed shortly before ingestion.

The compositions and solutions described herein may be bottled or packaged in, for example, glass bottles, plastic bottles and containers (e.g., polyethylene terephthalate or foil-lined ethylene vinyl alcohol), metal cans (e.g., coated aluminum or steel), lined cardboard containers, pouches, packs, wrappers, or any other packaging known to one of skill in the art. For example, a ready-to-drink beverage can be bottled or packaged in a unit that contains between 10-1000 mL of the beverage. For example, the packaging can contain 10, 20, 50, 100, 200, 300, 400, 500, 600, 700, 800, 900, or 1000 mL of the beverage. Alternatively, the packaging can contain 200, 250, 330, 350, 355, 375, 440, or 500 mL of the beverage. A ready-to-drink beverage can also be bottled or packaged in a unit that contains between 1-32 fluid ounces of beverage (e.g., the unit may contain 1, 2, 5, 6.75, 8, 8.3, 8.4, 8.45, 9.6, 10, 12, 15, 15.5, 16, 18.6, 20, 23, 24, or 32 fluid ounces). Where a shelf-stable composition or solution is desired, the packaging is appropriately sterilized before being filled by the pasteurized, ultra-pasteurized, or sterilized composition or solution. Where required for mutual stability of two or more components (for example if a component is unstable at low pH), the packaging may feature multiple containers that can be mixed shortly before ingestion or that can be consumed serially.

Routes of Administration and Dosage

The compositions of the present invention are formulated into acceptable dosage forms by conventional methods known to those of skill in the art. Actual dosage levels of the active ingredients in the compositions of the present invention may be varied so as to obtain an amount of the active ingredient which is effective to achieve the desired therapeutic response for a particular subject, composition, and mode of administration, without being toxic to the subject. The selected dosage level will depend upon a variety of pharmacokinetic factors including the activity of the particular compositions of the present invention employed, the route of administration, the time of administration, the rate of absorption of the particular agent being employed, the duration of the treatment, other drugs, substances, and/or materials used in combination with the particular compositions employed, the age, sex, weight, condition, general health and prior medical history of the subject being treated, and like factors well known in the medical arts. A physician or veterinarian having ordinary skill in the art can readily determine and prescribe the effective amount of the composition required. For example, the physician or veterinarian can start doses of the substances of the invention employed in the composition at levels lower than that required in order to achieve the desired therapeutic effect and gradually increase the dosage until the desired effect is achieved. In general, a suitable daily dose of a composition of the invention will be that amount of the substance which is the lowest dose effective to produce a therapeutic effect. Such an effective dose will generally depend upon the factors described above. Preferably, the effective daily dose of a therapeutic composition may be administered as one, two, three, four, five, six or more sub-doses administered separately at appropriate intervals throughout the day, optionally, in unit dosage forms.

The frequency of treatment may also vary. The subject can be treated one or more times per day (e.g., once, twice, three, four or more times) or every so-many hours (e.g., about every 2, 4, 6, 8, 12, or 24 hours). The composition can be administered 1, 2, or 3 times per 24 hours. The time course of treatment may be of varying duration, e.g., for two, three, four, five, six, seven, eight, nine, ten, or more days, two weeks, 1 month, 2 months, 4 months, 6 months, 8 months, 10 months, or more than one year. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Methods of Treatment

The compositions of the invention may be useful for improving or preserving exercise performance or recovery from exercise. Improving or preserving physical performance may comprise shortening the time to complete an exercise, e.g., a sprint or cycling exercise by the subject, increasing the maximal oxygen consumption ($VO_2$ max) in the subject, decreasing the fatigue of the subject, e.g., as measured by the Fatigue Index, or improving the energy level, improving the mood, or reducing the exertion and pain (e.g., perceived exertion and pain) of a subject. In some embodiments, the aforementioned improvement or preservation targets are determined relative to a reference standard.

In another aspect, the present invention features a method of improving recovery after exercise in a subject. Improving recovery may comprise reducing pain in a subject (e.g., reducing leg pain) or reducing inflammation in a subject.

In another aspect, the present invention features a method of reducing inflammation in a subject. In some embodiments, the inflammation occurs as a result of exercise.

EXAMPLES

Example 1: Effects of Exemplary Compositions on Exercise Performance

Overview

In order to study the effects of exemplary compositions on exercise performance and recovery, a study involving intermittent high intensity exercise was carried out on 20 healthy, active, college-aged men and women administered a beverage described herein.

Specific Aims

The goals of this study include determining of the effects of an exemplary composition on intense exercise performance, as well as to identify possible mechanisms responsible for the effects of said composition on exercise performance. Performance improvement may be associated with improved energy level, mental energy, and mood, and reduced perceived exertion and pain, with little or no effects on cardiovascular and/or metabolic function.

Methods

Twenty healthy, active, but untrained male and female subjects between the ages of 18 and 30 were recruited to participate in this study. Subjects were required to be in good general health with no recent musculoskeletal injuries, and absence of cardiovascular, respiratory, and metabolic disorders. Subjects were further required to maintain a normal state of hydration, e.g., by avoiding changes in caffeine consumption and dehydration-inducing substances (e.g., alcohol), maintain a normal diet, and avoid rigorous exercise 24 hours prior to the study. Subjects were screened using a health history questionnaire and signed an Informed Consent Form prior to participation. University of South Carolina Institutional Review Board approval was obtained prior initiation of the study for any cases requiring additional review.

The study was a randomized and counterbalanced, double-blind, placebo-controlled, cross-over design in which participants took part in both experimental (STA) and placebo conditions (PLA). The experimental treatment (STA) contained a mixture of ginger, cinnamon, *capsicum* in 50 ml (1.7 ounce) of a lime-juice vehicle. The placebo (PLA) was a vehicle control with no TRP activating component (1.7 ounce). The drinks were given to the participants immediately prior to the start of the exercise protocol (i.e., the initial sprint performance test). A second drink was provided during the rest period after the IHE session, 5 min prior to the time trial.

Exercise Protocols

The following tests and analyses were carried out on each subject:

Maximal Oxygen Consumption ($VO_2$ max): This test was conducted on a bicycle ergometer to determine the overall aerobic fitness level of subject and to set the individual workloads (% $VO_2$ max) for each subject during the controlled 45 min intermittent high intensity exercise session. The cycle test, which lasts between 8 to 15 minutes, progressively increased in difficulty during which inspired and expired air was analyzed for oxygen and carbon dioxide content. Subjects with a $VO_2$ max value between 40 ml/kg/min and 55 ml/kg/min were qualified for this study.

Maximal Sprint Cycling Performance—After a specified 5-min warm-up period, the overall exercise protocol began with a 30-s maximal sprint effort. Measurements was made from mean power output for 0-30 sec, peak power output (i.e., the maximum power output in Watts over a 5 s period), and mean power output for 0-10 s, 10-20 sec, and 20-30 s. The Fatigue Index, which is the rate of power decline during the test, was also calculated.

Intermittent High Intensity Exercise (IHE) Protocol: After the maximal sprint test (10 min), subjects completed a controlled IHE exercise session on a stationary bicycle ergometer (Monark) in a well-controlled laboratory setting (environmental chamber). The temperature and humidity was set at ambient conditions (i.e., 20° C. and 40% relative humidity). The controlled exercise protocol consisted of 45 min of repeated 5-minute bouts of 4-minute at ~60% $VO_2$ max followed by 1-minute at ~125% $VO_2$ max (sprints).

Cycling Time Trial (TT): After a 15-min rest period following completion of the IHE, subjects completed an approximately 10-minute time trial (e.g., race to the finish line) to complete a prescribed amount of work (i.e., distance) as fast as possible.

Experimental Measures

The following experimental measurements were taken for each subject prior to, during, and/or after each exercise protocol.

Body Weight: Nude body weight was measured using a precisely calibrated weighing scale before and after completion of each exercise trial to estimate of overall dehydration level.

Body Composition: The 7-site skinfolds technique was used to assess percent body fat and lean body mass during the preliminary session.

Heart Rate and Blood Pressure: In order to ensure subjects remain at safe limits and determine any benefits from the cooling towel, heart rate was continuously monitored using a heart rate monitor, and blood pressure was assessed at 10-minute intervals using an aneroid sphygmomanometer.

Body Core Temperature: Body core temperature (Tc) was recorded continuously throughout the exercise trial using rectal temperature (model 4600, YSI Precision Temperature Group, Dayton, Ohio). Subjects were not allowed to exceed a Tc>40° C./104° F. Rectal temperature is accepted as a valid and reliable measure of Tc.

Ratings of Perceived Exertion: Perceived exertion ratings were assessed using a 20-point Borg scale at a 10-minute interval throughout the exercise session.

Leg Muscle Pain: Leg-muscle pain intensity was measured immediately after each of the initial sprint performance test, at the end of the 1 min sprints during IHE, and immediately after TT using a validated 10-point scale.

Mood State: The Profile of Mood State (POMS) questionnaire was used to assess the mood states prior to taking the supplement and immediately before IHE and TT. The self-report scales are a collection of tools that allow for the quick assessment of transient, fluctuating feelings, and enduring affect states. Exemplary scale scores include: Anger-Hostility, Confusion-Bewilderment, Depression-Dejection, Fatigue-Inertia, Tension-Anxiety, and Vigor-Activity. Each was determined separately and a Total Mood Disturbance score was assigned, which is a function of these six scale scores.

Blood collection: An intravenous catheter was inserted into a forearm vein prior to testing. Then 5-min prior to experimental testing, 10 ml of blood was collected via the catheter and then again at 15-minute intervals through the exercise session. Blood samples were analyzed for markers of metabolic function (e.g., glucose, lactate), muscle damage (e.g., creatine kinase) and inflammation (e.g., inflammatory cytokines IL-6, IL-10, IL-lra protein and leukocyte gene expression).

General Procedures

Information Session: Before starting the protocol, subjects attended a meeting with the study coordinator to complete informed consent and health history questionnaire.

Preliminary Session: Both preliminary and experimental sessions were held in the laboratory of Public Health Research Center located at the University of South Carolina. Subjects first attended the preliminary session for height, weight and body composition assessment followed by a maximal $VO_2$ test on a stationary cycle ergometer. For the second preliminary session, 60% and 125% $VO_2$ max workloads were set and validated on the bicycle ergometer, and participants became familiarized with the exercise protocol and experimental procedures.

Experimental Sessions I Data Collection: Qualified subjects were then randomized and counterbalanced to either experimental (STA) or control (PLA) treatments for the 1st trial. The 2nd trial (opposite treatment) was done within 5-7 days after the first trial.

Prior to the testing day, subjects were instructed to maintain normal exercise habits and refrain from vigorous exercise 24 hours prior to the session. They were also asked to abstain from consumption of any caffeinated beverage and dehydration-inducing substances such as alcohol 12 hours prior to the trial and to fully hydrate themselves (16 oz water) 1-2 hr before reporting to the lab the day of the trial. Immediately prior to the start of exercise trial, the STA or PLA drink (1.7 oz) was given to the subjects. They were asked to consume the drink within 2 min, first swishing the solution around their mouth and then swallowing. Subjects were provided water to consume every 15 min (3.5 ml/kg body weight) during IHE to maintain adequate hydration.

Data Analysis: Statistical analysis was performed with SPSS for Windows (SPSS, Chicago, Ill.). A two-way repeated measures ANOVA was used to determine the significance of differences between means by condition, time and their interaction. A two-tailed alpha level of 0.05 was used for all significance tests.

Results

Consistent beneficial trends were observed for subjects that received the experimental drink (STA) across several tested variables. For example, subjects that drank STA exhibited greater mean power (p=0.09), total power (p=0.09), and 5 s interval power (p=0.09) during the 30 s maximal sprint test. In addition, 14 of 19 subjects (p=0.20) demonstrated a greater time trial distance, and overall, the subjects that consumed STA had lower ratings of leg muscle pain sensation during the course of the experimental sessions (treatment×time effect, p=0.17). In addition, subjects receiving STA had improved mood over the course of the test (p=0.20).

These results support a central finding that exemplary compositions (e.g., STA and others described herein) may work through stimulation of the CNS, as no differences were seen between STA and PLA on markers of cardiovascular, metabolic, and inflammatory function. In addition, these results suggest that subjects consuming the exemplary compositions described herein (e.g., STA) comprising TRPV1 and TRPA1 agonists may improve performance during exercise (e.g., intermittent, high-intensity exercise) with no apparent adverse side effects.

EQUIVALENTS

The disclosures of each and every patent, patent application, and publication cited herein are hereby incorporated herein by reference in their entirety. While this disclosure has been described with reference to specific aspects, it is apparent that other aspects and variations may be devised by others skilled in the art without departing from the true spirit and scope of the disclosure. The appended claims are intended to be construed to include all such aspects and equivalent variations. Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference.

While this disclosure has been particularly shown and described with references to preferred embodiments thereof, it will be understood by those skilled in the art that various changes in form and details may be made therein without departing from the scope of the disclosure encompassed by the appended claims.

The invention claimed is:

1. A method for improving or preserving physical performance during exercise in a subject, wherein the method comprises orally administering to the subject a composition comprising *capsicum*, ginger, cinnamon, and an excipient, wherein improving or preserving physical performance during exercise in a subject is increasing the energy of the subject, improving the mood of the subject, reducing the exertion of the subject, or reducing the pain of the subject, relative to a reference standard.

2. The method of claim 1, wherein the method further comprises administering to the subject an amount of composition in the range of 10 mL to 1000 mL.

3. The method of claim 1, wherein the composition is administered to the subject prior to commencement of exercise.

4. The method of claim 1, wherein:
(a) the amount of *capsicum* in the composition is in the range of 0.001% (w/w) to 1% (w/w); or
(b) the amount of ginger in the composition is in the range of 0.001% (w/w) to 1% (w/w); or
(c) the amount of cinnamon in the composition is in the range of 0.001% (w/w) to 1% (w/w).

5. The method of claim 1, wherein the excipient is selected from the group consisting of an antioxidant, a binder, a coloring agent, a disintegrant, an emulsifier, a flavoring agent, a lubricant, a pH-adjusting agent, a preservative, a surfactant, a sweetener, and viscosity modifier.

* * * * *